United States Patent [19]
Scott

[11] Patent Number: 5,236,450
[45] Date of Patent: Aug. 17, 1993

[54] HEART VALVE HOLDER-ROTATOR

[75] Inventor: Peters T. Scott, Georgetown, Tex.

[73] Assignee: Carbon Implants, Inc., Austin, Tex.

[21] Appl. No.: 893,656

[22] Filed: Jun. 4, 1992

[51] Int. Cl.⁵ .......................... A61F 2/24; A61F 2/54
[52] U.S. Cl. .......................................... 623/2; 623/66
[58] Field of Search ............................... 623/2, 3

[56] References Cited

U.S. PATENT DOCUMENTS

| | | | |
|---|---|---|---|
| 4,512,471 | 4/1985 | Kaster et al. | 623/2 X |
| 4,585,453 | 4/1986 | Martin et al. | 623/2 |
| 4,679,556 | 7/1987 | Lubock et al. | 128/303 |
| 4,683,883 | 8/1987 | Martin | 128/303 |
| 4,702,250 | 10/1987 | Ovil et al. | 128/334 |
| 5,041,130 | 8/1991 | Cosgrove et al. | 623/2 |

*Primary Examiner*—Randall L. Green
*Assistant Examiner*—Dinh X. Nguyen
*Attorney, Agent, or Firm*—Fitch, Even, Tabin & Flannery

[57] ABSTRACT

A heart valve holder is provided for holding a heart valve prothesis including an orifice ring having an aperture with a circumferential surface, comprising: a body having a longitudinal axis; a first lever section having a first insertion end and resiliently attached to the body along a first flexure region having a first flexure axis for selectively engaging the heart valve prothesis; and a second lever section having a second insertion end and resiliently attached to the body along a second flexure region having a second flexure axis parallel to the first flexure axis for selectively engaging the heart valve prothesis. The body and the first and second lever sections include receiving means for receiving a flexible tensile member to secure engagement of the first and second lever sections to the heart valve prosthesis by flexing the first and second flexure regions so that the first and second insertion ends abut the circumferential surface of the aperture.

18 Claims, 4 Drawing Sheets

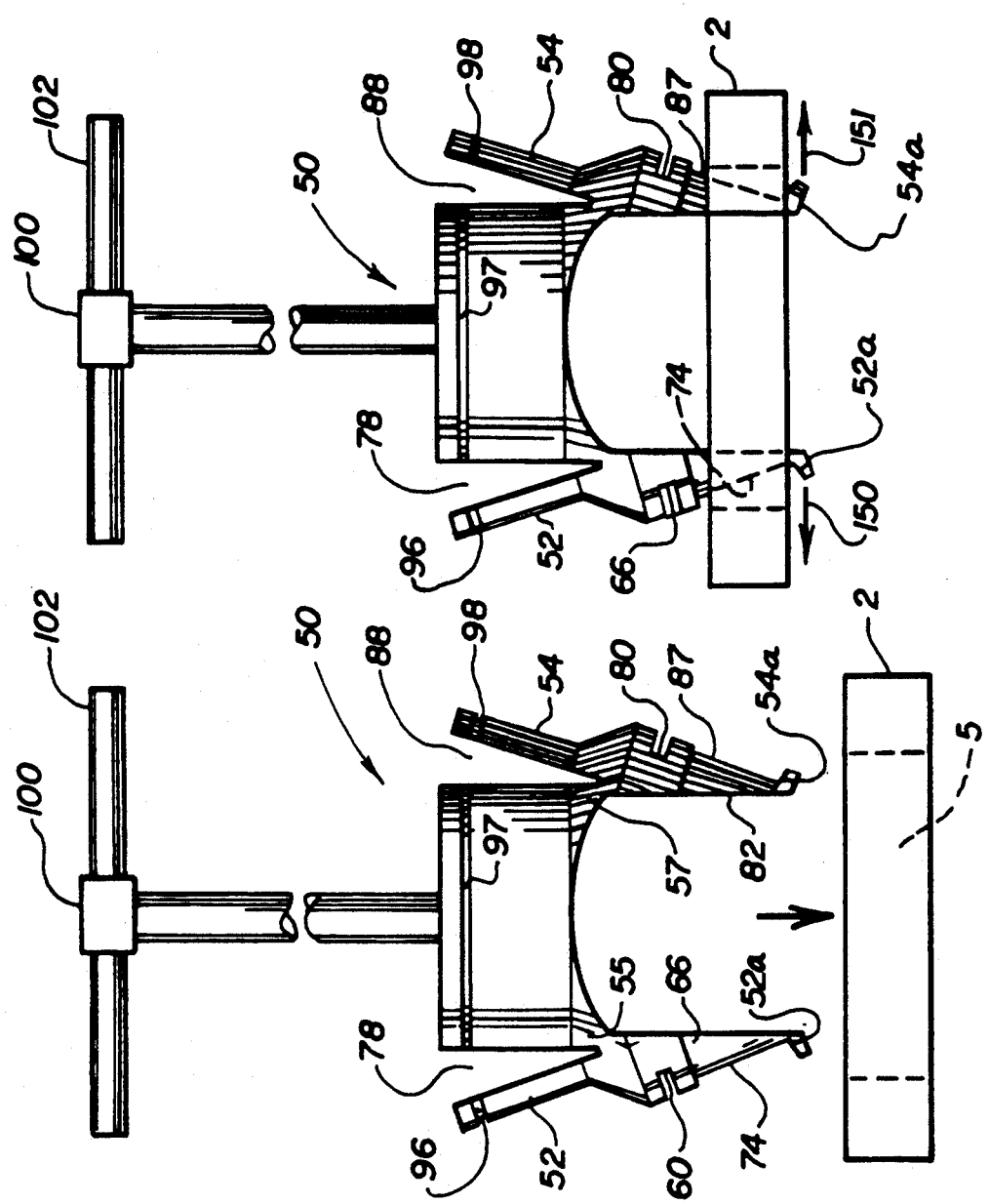

HEART VALVE HOLDER-ROTATOR

The present invention is directed to a device for holding a mechanical heart valve prosthesis both during shipping and implantation.

BACKGROUND OF THE INVENTION

The use of surgically implanted mechanical heart valves has become widespread and even routine. One type of mechanical heart valve in common use is described in U.S. Pat. No. 4,276,658 and is depicted in FIG. 1 which shows a valve 2a comprising an orifice ring 4a positioned within an implanting flange, or sewing ring 6a. An occluder, in the form of one or two leaflets 7a, is pivotally supported by a pivot mechanism (not shown) within the orifice ring 4a to alternately open and close a blood flow passageway through a passageway 5a of the orifice ring having an interior surface 11a. The occluder acts as a check valve to prevent regurgitation of blood through the orifice ring 4a when pumping action of the heart produces localized back pressure. The orifice ring 4a is formed with upstanding projections 9a having flat inside surface sections 10a on which are located part of the pivot mechanism. The flat surface sections 10a form part of the otherwise curvilinear surface 11a.

Specialized tools have been developed to assist in the implantation of mechanical heart valves of the type described in the '658 patent. An effective tool should be capable of both holding the valve and allowing it to be manipulated at the implantation site in order to properly position it. The tool should also provide easy engagement with and disengagement from the valve without damaging the leaflets and/or dislodging them from the pivot mechanism.

FIG. 1 also illustrates an example of a tool for holding the type of valve described above which includes a body 12 and a jaw 14 linked by flexible hinges 16 (only one is shown). Flanges 18 and 20 on the body 12, and flanges 22 and 24 on a jaw 14 form arcuate channels 19 and 23, respectfully, which are inserted through the passageway 5a of the orifice ring 4a to abut the inner circumferential surface 11a so as to engage the valve. A filament 26, when tied tightly around the body 12 and jaw 14, holds the jaw and body extended so that the valve is securely engaged within the arcuate channels. Cutout surfaces, or reliefs 28 and 30 in the body 12 and jaw 14, respectively, provide clearance to fit about the projections 9a. When the filament 26 is cut, the body 12 and jaw 14, only linked by flexible hinges 16, may be manipulated to disengage the arcuate channels 19 and 23 from orifice ring 4a, thereby allowing the tool to be separated and retracted from the valve.

A potential disadvantage of this type of tool is that after the filament 26 is cut, the body 12 and/or jaw 14 may flail about and pinch a sealing surface of the valve or even cause an occluder to become dislodged from the pivot mechanism.

For convenience, valve prostheses and their associated holders are commonly assembled by the manufacturer and shipped as assemblies in sterile enclosures. To prevent damage to the valve during shipping and handling, the assembly must form a stable structure.

Therefore, there is a need for a tool for securely holding a heart valve prosthesis and rotating it within the surrounding sewing ring which may easily be selectively separated from the valve. A need also exists for a tool that can be released and withdrawn from the valve without damaging it. Such a tool should also be capable of adequately supporting the valve in order to prevent it from being damaged during shipment.

SUMMARY OF THE INVENTION

A heart valve holder is provided for holding a heart valve prosthesis including an orifice ring having a passageway defined by an inside circumferential surface which is shaped to support and guide a pair of leaflets between open and closed positions. The holder has two diametrically opposed movable sections which are resiliently attached to and pivot in small arcs about a center section.

More particularly, a heart valve holder is provided for holding a heart valve prosthesis including an orifice ring having an aperture with a circumferential surface, comprising: a body having a longitudinal axis; a first lever section having a first insertion end and resiliently attached to the body along a first flexure region having a first flexure axis for selectively engaging the heart valve prosthesis; a second lever section having a second insertion end and resiliently attached to the body along a second flexure region having a second flexure axis parallel to the first flexure axis for selectively engaging the heart valve prosthesis; and where the body, and the first and second lever sections further include receiving means for receiving a flexible tensile member to secure engagement of the first and second lever sections to the heart valve prosthesis. The holder may also include a flexible tensile member to secure the first and second lever sections to the heart valve prosthesis by flexing the first and second flexure regions so that the first and second insertion ends abut the circumferential surface of the aperture.

The present invention also includes the combination of the heart valve holder, as described above, engaging a heart valve prosthesis held by a flexible tensile member wrapped around the first and second lever sections and the body which secures engagement of the first and second lever sections to the heart valve prosthesis by flexing living hinges which form the first and second flexure regions so that the first and second insertion ends abut the inside circumferential surface of the orifice ring.

An advantage of the present invention is that it provides a tool that securely engages a heart valve prosthesis to facilitate implantation of the valve, yet which may be easily and selectively separated from the valve without damaging it. These and other advantages of the invention will be more appreciated upon review of the specification, drawings, and claims.

BRIEF DESCRIPTION OF THE DRAWINGS

FIG. 3 is a front elevation view of the heart valve holder of FIG. 2 shown being inserted into a heart valve prosthesis (shown schematically) with a tool.

FIG. 4 is a front elevation view of the heart valve holder and tool of FIG. 3 shown positioned within the heart valve.

Throughout the several views, like reference numbers are used to designate like components and features.

DETAILED DESCRIPTION OF THE PREFERRED EMBODIMENT

Figures 1, 2:
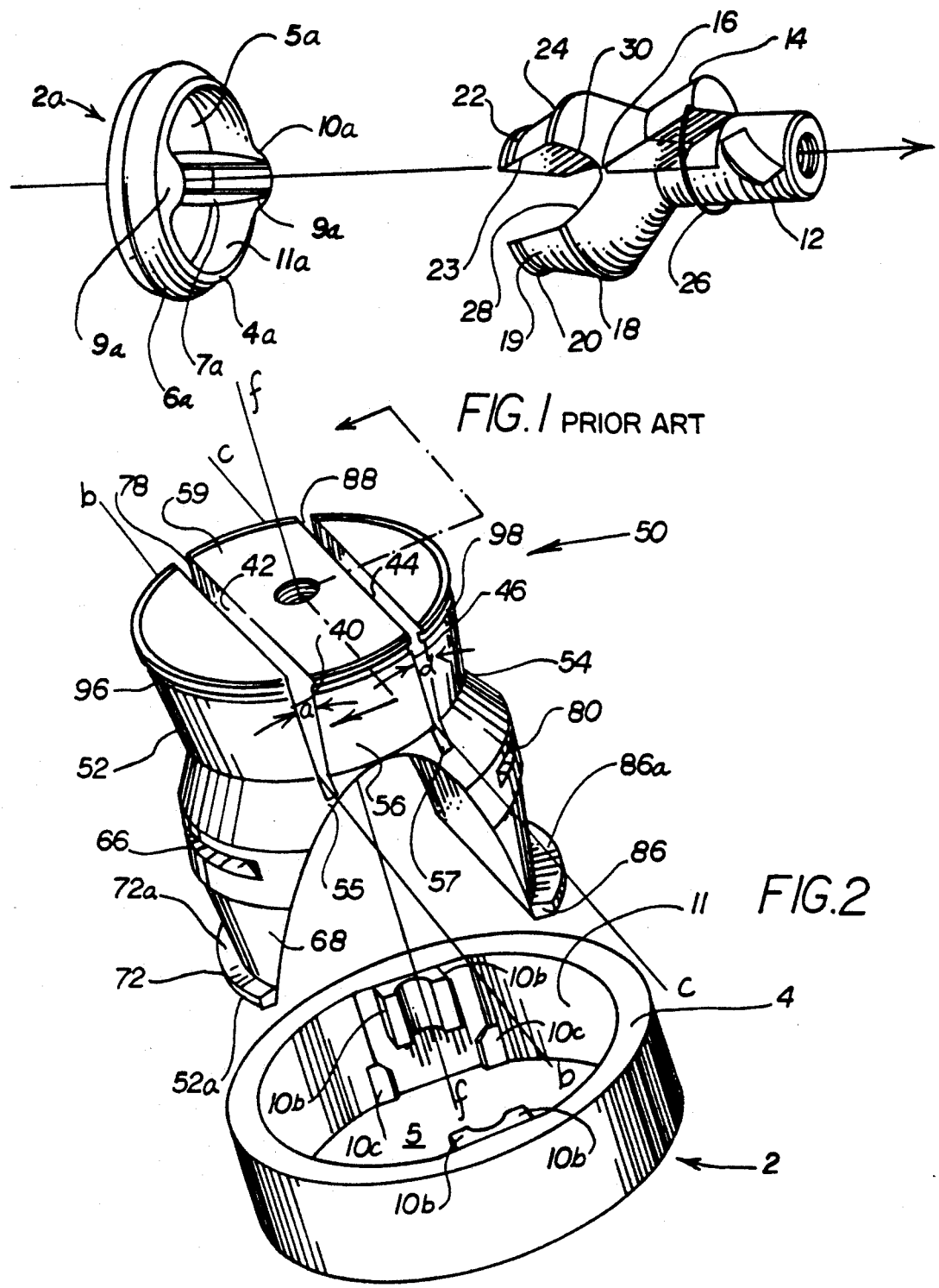
FIG. 1 is a perspective view of a prior art heart valve prosthesis and tool for holding the valve.
FIG. 2 is a three-quarter, perspective top view of a heart valve holder embodying various features of the present invention.

FIG. 2 is a perspective, three-quarter top view illustrating a heart valve holder 50 embodying various features of the present invention for holding a heart valve prosthesis 2. Although the holder 50 could be used with a heart valve prosthesis the type described in the '658 patent, the disclosure of which is incorporated herein by reference, the holder is illustrated in connection with a valve body or orifice ring 4 in which the leaflets (not shown) are guided by projections 10b and 10c which extend inwardly from the inside circumferential surface. Holder 50 includes lever sections 52 and 54 resiliently attached to a main body 56 at flexure regions 55 and 57, respectively. Flexure region 55 is provided by a living hinge along axis b—b between the lever section 52 and the body 56. Similarly, the flexure region 57 is provided by a living hinge along is c—c between the lever section 54 and body 56, where the axes b—b and c—c are parallel to each other. The flexure region 55 may be resiliently and angularly deflected to reduce an angle a, between an inner flat surface 40 of the lever section 52 and a flat surface 42 of the body 56, where the flat surface 42 is substantially parallel to the longitudinal center axis f—f of the body 56. Likewise, the flexure region 57 may be resiliently and angularly deflected to reduce an angle d, between a flat surface 44 of lever section 54 and a flat surface 46 on the opposite side of the body 56, which flat surface 46 is also substantially parallel to the longitudinal center axis f—f of the body 56. Reduction of the angles a and d when holder 50 is positioned within the orifice ring 4 results in engagement of the holder with the orifice ring.

When the flexure regions 55 and 57 are in their unstressed, as-molded orientation, the angles a and d, are normally between about 10° and about 15°, so that the distance g (FIG. 5) between the outer surfaces of insertion lower ends 52a and 54a of the lever sections 52, 54 allows simultaneous free passage of the ends through the passageway 5 of the orifice ring 4. By thereafter deflecting the flexure regions 55 and 57 to decrease the angles a and d, the lever sections 52 and 54 are caused to engage the heart valve 2, as shown in FIG. 5.

Figure 5:
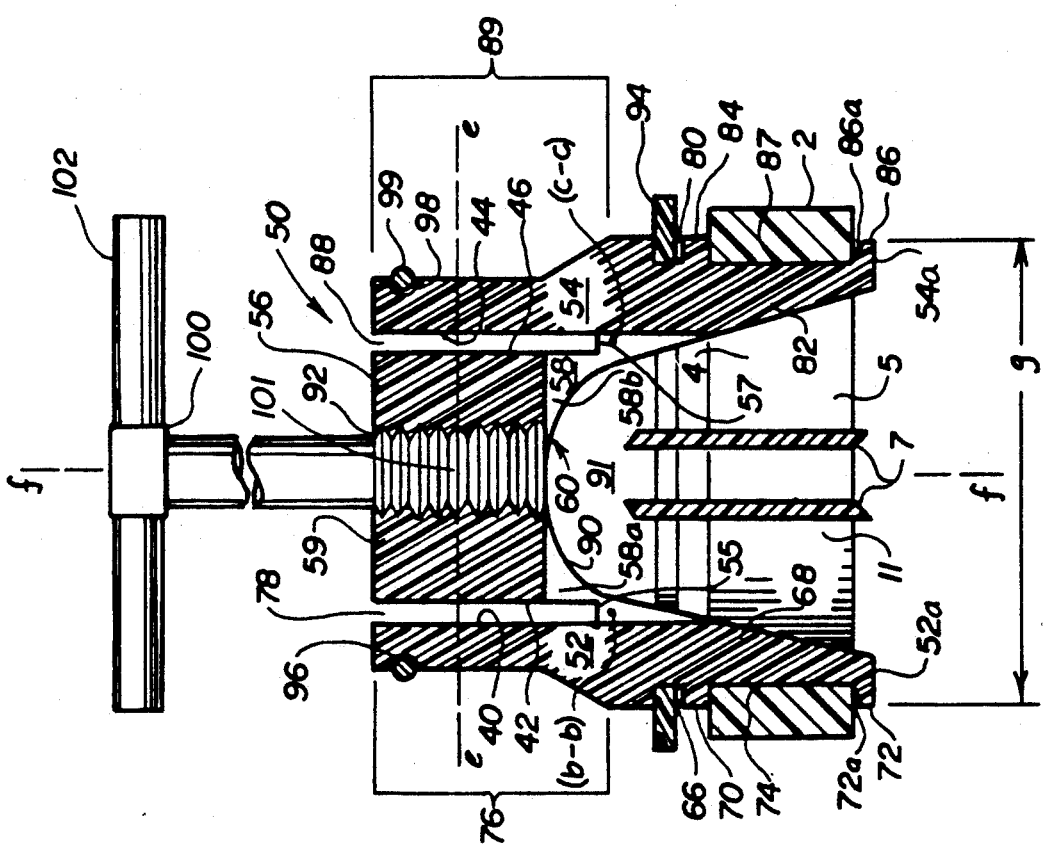
FIG. 5 is a front cross-sectional view of the heart valve holder of FIG. 2 shown holding a heart valve prosthesis with the leaflets also shown schematically.

Still referring to FIG. 5, the lever sections 52 and 54 are positioned about body 56 so as to provide diametrically opposed engagement of valve 2 as they are extended in the passageway 5 of the orifice ring 4. While the preferred embodiment is described as having two lever sections, it is to be understood that the scope of the invention comprehends that additional lever sections may be employed so long as they may be positioned within orifice ring 4 in a manner which provides secure engagement of the valve without contacting the leaflets 7 which are diagrammatically shown therein.

Figure 7:
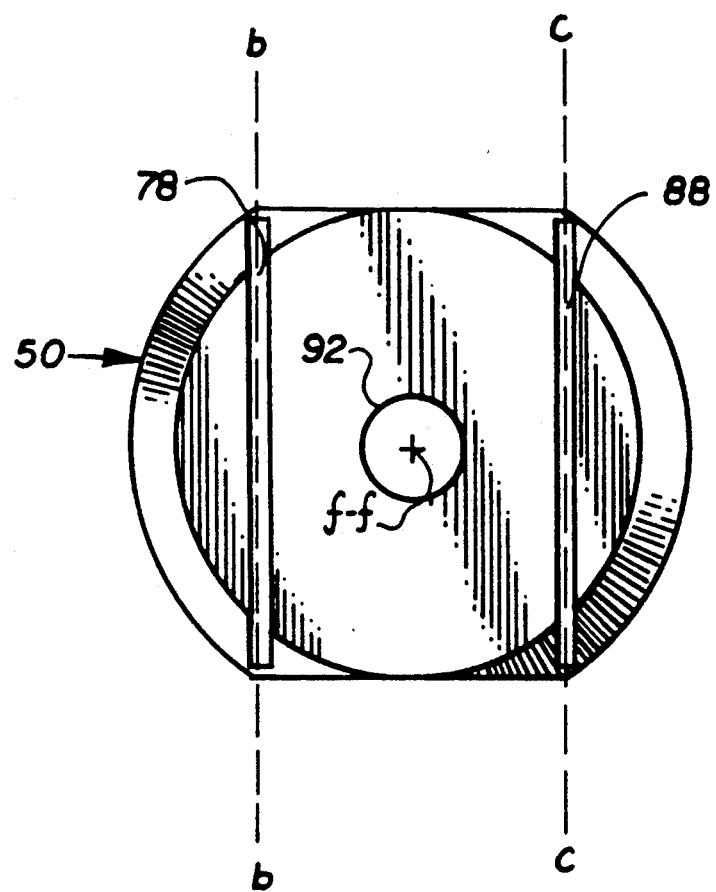
FIG. 7 is a plan view of the heart valve holder of FIG. 5 without a supporting C-shaped shelf support.

Referring to FIGS. 2 and 7, flexure axes b—b and c—c define a plane perpendicular to longitudinal axis f—f of body 56, and are separated by a fixed distance preferably centered about longitudinal axis f—f. This feature permits the holder 50 to engage and disengage the valve 2 in a manner which minimizes any potential impingement or pinching of the leaflets 7 or any other component of the valve 2 because the positions of the lever sections 52 and 54 with respect to body 56 are constrained such that they are capable of only slight deflection in a small arc. Furthermore, the lever sections 52 and 54 cannot flail about upon release or disengagement of the holder 50 from valve 2. The manner in which the lever sections 52 and 54 are attached to the body 56 allows the surgeon to precisely control the position of the holder 50 with respect to the valve while the holder is being withdrawn from the passageway 5 of orifice ring 4.

In the preferred embodiment, the holder 50 is preferably injection-molded in one piece from a material capable of being sterilized, such as nylon, TEFLON ®, or DELRIN ®. The holder 50 may have a substantially circular cross-section in a plane defined by line e—e, which is perpendicular to the longitudinal axis f—f of the holder 50, as shown in FIG. 5. Furthermore, the holder 50 may have a substantially circular cross-sectional area as also shown in FIG. 7, in planes parallel to the plane defined by line e—e. One piece construction enables holder 50 to be manufactured relatively easily and inexpensively.

Figure 6:
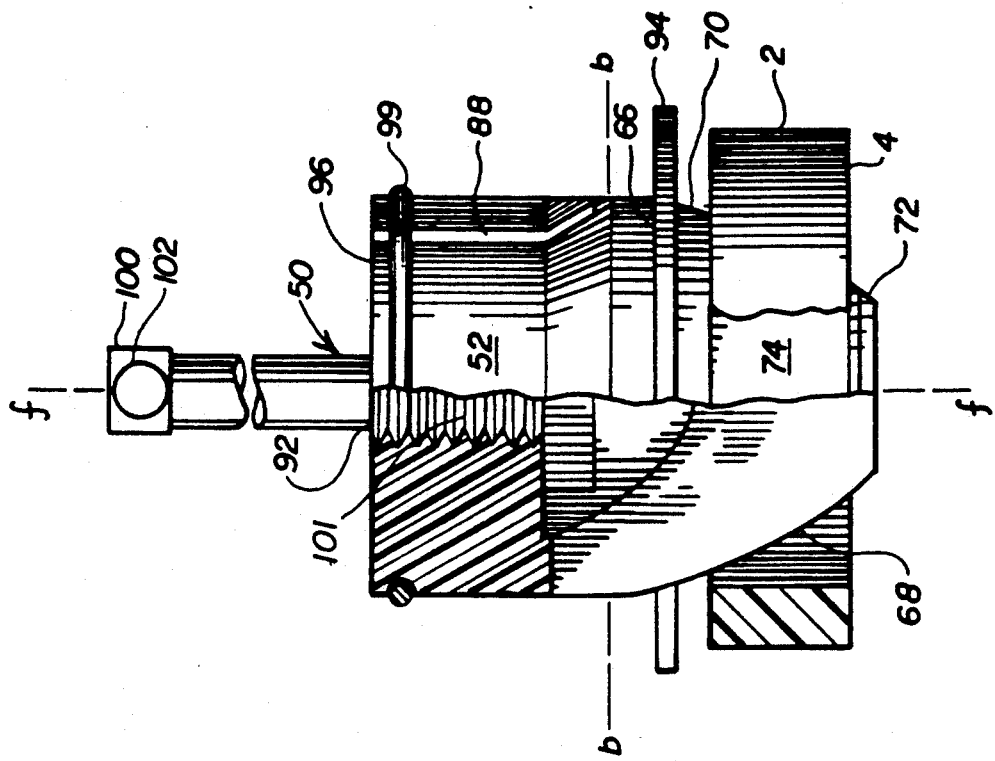
FIG. 6 is a side partial elevation, partial cross-sectional view of the heart valve holder presented in a view plane 90 degrees from the view of FIG. 5.

Referring to FIGS. 5 and 6 collectively, the outer surface of the lever section 52 includes a slot 66. The lever section 52 also includes a tapered section 68 having arcuate flanges 70 and 72 which define an arcuate channel 74, and an actuation arm region 76 separated from most of the main body 56 by a slot 78 which lies between a flat surface 40 of the lever section 52 and a flat surface 42 of the body 56, which are preferably substantially parallel in the operative position (FIG. 5).

The outer surface of the lever section 54 includes a slot 80 which is symmetrical with slot 66. The lever section 54 also includes a tapered section 82 having arcuate flanges 84 and 86 which define an arcuate channel 87 symmetrical with the channel 74 and includes an actuation arm region 89 which is separated from most of the body 56 by a slot 88, symmetrical with the slot 78. The slot 88 is defined by the flat surface 46 of the body 56 and the flat surface 44 of the lever section 54. Thus, it can be seen that slots 78 and 88 are spaced apart from each other, are located symmetrically about the longitudinal axis f—f, and extend from the top surface 59 of the body 56 to the living hinges forming the flexure regions 55 and 57.

The upper or interior surfaces 72a and 86a of the diametrically opposed flanges 72 and 86, respectively, are tapered downwardly and outwardly about 5° to facilitate engagement of the channels 74 and 88 with the interior circumferential surface 11 of the orifice ring 4. The lever sections 52 and 54 also each have an upper groove 96 and 98, respect of which are aligned with similar grooves 97 (FIGS. 3 and 4) in the body 56, to form a 360° cavity, in which a flexible tensile member 99 is held as described further herein. The grooves 97 (only one is shown), as depicted in FIGS. 3 and 4, which together with grooves 96 and 98 define the 360° cavity or annular channel are diametrically opposed. The flexible tensile member 99 may be a thread or suture. The channels 74 and 87 are each preferably slightly wider, as for example, by about 0.020 inch, than the height of the orifice ring 4 to facilitate engagement of the holder to the orifice ring.

Still referring to FIGS. 5 and 6, reliefs 58a and 58b at an end 60 of the holder 50 extend into the body 56 as well as into tapered sections 68 and 82 to form a bore 58.

Although relatively shallow, the bore 58 provides clearance for the leaflets 7 of the valve 2 when the valve is engaged by the lever sections 52 and 54. Curved under surfaces 90 at diametrically opposed locations also provide clearance for the leaflets.

Engagement of the holder 50 to the valve 2 is described below with reference to FIGS. 3, 4, and 5. The tapered sections 68 and 82 are inserted through the passageway 5 of the orifice ring 4 until the channels 74 and 87 are substantially positioned to align with the orifice ring. The overall lengths of the arc lengths of the flanges 72 and 86, and of the arc lengths of the flanges 84 and 86, are sized to easily fit through the passageway 4 of the heart valve 2. Then, tensile member 99 is positioned within grooves 96, 97, and 98, and tied tightly enough so that the actuation arm regions 76 and 89 near the upper end 59 of body 56 are inwardly and angularly displaced towards one another to reduce the angles a and d, respectively. Such inward rotation of the actuation arm regions causes lower ends 52a and 54a to be outwardly displaced in the direction of arrows 150 and 151 (FIG. 4) so that channels 74 and 87 engage and abut the inner circumferential surface 11 of the orifice ring 4. When tied around the body 50, the tensile member 99 prevents flexure regions 55 and 57, and hence actuation arm regions 76 and 89 from returning to their unstressed, originally molded orientation which would result in disengagement of the holder 50 from the heart valve prosthesis 2.

It is expected that the holder 50 and the valve 2 will be packaged and shipped as a sterilized assembly with valve 2 remaining secured within the holder. During shipping, holder 50 is supported by C-shaped shelf support 94 which slides into slots 66 and 80 of lever sections 52 and 54, respectively. The C-shaped shelf support 94 is inserted into the slots 66 and 80 when the holder 50 is placed in the packaging, not shown.

As shown in FIG. 5, the body 56 may also include a tool 100 mounted to the top surface 59 of the body 56. The tool 100 includes a handle 102 which facilitates manipulation of the tool. The tool 100 permits the combination of heart valve holder 50 and heart valve prosthesis 2 to be precisely manipulated by a surgeon during implantation of the valve. By way of example to accommodate the tool 100, body 56 may include a tapped hole 92 having a longitudinal axis coincident with axis f—f extending from the top surface 59 of the body. The tool 100 may have a threaded end 101 which threadably engages hole 92. Rotation of the heart valve 2 within the suture ring is accomplished by holding the handle 102 and rotating tool 100 so that tapered sections 68 and 82 engage and transmit torque to flat surfaces within the passageway 5 of orifice ring 4, (similar to the flat surfaces 10a shown in FIG. 1).

Rather than being threaded to body 56, the tool 100 and body may be configured so that they attach to one another using a snap fit, detente, or interference fit, as would be well known by those skilled in the art.

As soon as the assemblage is removed from the packaging, and prior to implantation of the heart valve prosthesis 2, the C-shaped shelf support 94 is withdrawn from the slots 66 and 80 and discarded. Then after the valve is installed in the patient's heart, the surgeon releases holder 50 from valve 2 by cutting the tensile member 99. When the tensile member 99 is cut, the flexure regions 55 and 57 return to their unstressed, relaxed states, resulting in a decrease in the distance g (FIG. 5) between lower ends 52a and 54a. Then the assembly of tool 100 and holder 50 may be withdrawn either straightaway or in any convenient direction out from the passageway 5 of the valve 2 with ample clearance being provided for the leaflets.

Thus it may be appreciated that a holder for a heart valve prosthesis has been provided that fully meets the above-stated objectives. Although the holder has been described in terms of a preferred embodiment, it is to be understood that the scope of the invention includes all modifications and constructions falling within the scope of the appended claims.

What is claimed is:

1. A heart valve holder for holding a heart valve prosthesis including an orifice ring having an aperture with a circumferential surface, comprising:
    a body having a longitudinal axis;
    a first lever section having a first insertion end and resiliently attached to said body along a first flexure region having a first flexure axis for selectively engaging said heart valve prosthesis;
    a second lever section having a second insertion end and resiliently attached to said body along a second flexure region having a second flexure axis parallel to said first flexure axis for selectively engaging said heart valve prosthesis; and
    said body, and said first and second lever sections further including receiving means for receiving a flexible tensile member to secure engagement of said first and second lever sections to said heart valve prosthesis.

2. The heart valve holder of claim 1 wherein:
    said first and second flexure axes are separated by a fixed distance centered about said longitudinal axis and define a plane perpendicular to said longitudinal axis of said body.

3. The heart valve holder of claim 2 wherein:
    said first and second insertion ends are normally disposed with respect to one another so that said first and second ends can both pass simultaneously through said aperture of said orifice ring.

4. The heart valve holder of claim 3 wherein:
    said first and second lever sections engage said heart valve prosthesis by flexing said first and second flexure regions so that said first and second insertion ends engage said circumferential surface of said aperture.

5. The heart valve holder of claim 4 wherein:
    said first lever section has a first arcuate channel for engaging said circumferential surface of said aperture; and
    said second lever section has a second arcuate channel for engaging said circumferential surface of said aperture.

6. The heart valve holder of claim 5 wherein said body has a first end and said valve holder further includes:
    a first slot between said body and said first lever section extending from said first end of said body to said first flexure region; and
    a second slot between said body and said second lever section diametrically opposed to said first slot and extending from said first end of said body to said second flexure region.

7. The heart valve holder of claim 5 wherein said first and second lever sections each include reliefs for accommodating said heart valve prosthesis.

8. The heart valve holder of claim 5 wherein said receiving means includes grooves in each of said first and second lever sections and said body, said grooves defining a common annulus.

9. The heart valve holder of claim 1 further including:
a tool mounted to said body for positioning said body.

10. In combination, a heart valve holder for holding a heart valve prothesis during implantation, comprising:
a heart valve prothesis including an orifice ring having an aperture with an inside circumferential surface; and
a heart valve holder including:
a body having a longitudinal axis;
a first lever section having a first insertion end and resiliently attached to said body along a first flexure region having a first flexure axis for selectively engaging said heart valve prosthesis;
a second lever section having a second insertion end and resiliently attached to said body along a second flexure region having a second flexure axis parallel to said first flexure axis for selectively engaging said heart valve prosthesis;
a flexible tensile member;
said body, and said first and second lever sections further including receiving means for engaging said flexible tensile member to secure said first and second lever sections to said heart valve prosthesis.

11. The heart valve holder of claim 10 wherein:
said first and second flexure axes are separated by a fixed distance centered about said longitudinal axis and define a plane perpendicular to said longitudinal axis of said body.

12. The heart valve holder of claim 11 wherein:
said first and second insertion ends are normally disposed with respect to one another so that said first and second ends can both pass simultaneously through said aperture of said orifice ring.

13. The heart valve holder of claim 12 wherein:
said first and second lever sections engage said heart valve prosthesis by flexing said first and second flexure regions so that said first and second insertion ends engage said circumferential surface of said aperture.

14. The heart valve holder of claim 13 wherein:
said first lever section has a first arcuate channel for engaging said circumferential surface of said aperture; and
said second lever section has a second convex arcuate channel for engaging said circumferential surface of said aperture.

15. The heart valve holder of claim 14 wherein said body has a first end and said valve holder further includes:
a first slot between said body and said first lever section extending from said first end of said body to said first flexure region; and
a second slot between said body and said second lever section diametrically opposed to said first slot and extending from said first end of said body to said second flexure region.

16. The heart valve holder of claim 14 wherein said first and second lever sections each include reliefs for accommodating said heart valve prosthesis.

17. The heart valve holder of claim 14 wherein said receiving means includes grooves in each of said first and second lever sections and said body, said grooves defining a common annulus.

18. The heart valve holder of claim 10 further including:
a tool mounted to said body for positioning said body.

* * * * *

UNITED STATES PATENT AND TRADEMARK OFFICE
CERTIFICATE OF CORRECTION

PATENT NO. : 5,236,450
DATED : August 17, 1993
INVENTOR(S) : T. Scott Peters

It is certified that error appears in the above-indentified patent and that said Letters Patent is hereby corrected as shown below:

On the title page, item (75) inventor's name, change:
"Peters T. Scott" to --T. Scott Peters--.

IN THE ABSTRACT: Line 2, correct the spelling of "prosthesis".

Column 2, line 8, correct the spelling of "prosthesis".

Column 7 (Claim 10), lines 6 and 7, correct the spelling of "prosthesis".

Signed and Sealed this

Nineteenth Day of July, 1994

Attest:

BRUCE LEHMAN

*Attesting Officer*  Commissioner of Patents and Trademarks